US006800096B1

(12) United States Patent
Legrand et al.

(10) Patent No.: US 6,800,096 B1
(45) Date of Patent: Oct. 5, 2004

(54) COMPOSITION, PROCESS AND KIT FOR BLEACHING KERATIN FIBERS COMPRISING AT LEAST ONE THICKENING POLYMER WITH AN AMINOPLAST-ETHER SKELETON

(75) Inventors: Frédéric Legrand, Billancourt (FR); Delphine Allard, Colombes (FR)

(73) Assignee: L'Oreal S.A., Paris (FR)

( * ) Notice: Subject to any disclaimer, the term of this patent is extended or adjusted under 35 U.S.C. 154(b) by 220 days.

(21) Appl. No.: 10/149,009

(22) PCT Filed: Nov. 10, 2000

(86) PCT No.: PCT/FR00/03141

§ 371 (c)(1),
(2), (4) Date: Aug. 28, 2002

(87) PCT Pub. No.: WO01/41725

PCT Pub. Date: Jun. 14, 2001

(30) Foreign Application Priority Data

Dec. 8, 1999 (FR) .......................................... 99 15484

(51) Int. Cl.$^7$ ................................................. A61K 7/06
(52) U.S. Cl. ...................... 8/401; 8/552; 8/602; 8/606; 8/101; 8/107; 8/111; 524/590; 525/406
(58) Field of Search ........................... 8/401, 552, 602, 8/606, 101, 107, 111; 524/590; 525/406

(56) References Cited

U.S. PATENT DOCUMENTS

| | | | |
|---|---|---|---|
| 2,261,002 A | 10/1941 | Ritter ......................... 260/570 |
| 2,271,378 A | 1/1942 | Searle ......................... 167/22 |
| 2,273,780 A | 2/1942 | Dittmar ....................... 260/28 |
| 2,375,853 A | 5/1945 | Kirby et al. ................. 266/588 |
| 2,388,614 A | 11/1945 | Kirby et al. ................. 167/22 |
| 2,454,547 A | 11/1948 | Bock et al. .............. 260/367.6 |
| 2,528,378 A | 10/1950 | Mannheimer ........... 260/209.6 |
| 2,781,354 A | 2/1957 | Mannheimer ........... 260/349.6 |
| 2,961,347 A | 11/1960 | Floyd ......................... 117/141 |
| 3,206,462 A | 9/1965 | McCarty ................. 260/256.4 |
| 3,227,615 A | 1/1966 | Korden ..................... 167/87.1 |
| 3,632,559 A | 1/1972 | Matter ........................ 260/78 |
| 3,874,870 A | 4/1975 | Green et al. .................. 71/67 |
| 3,917,817 A | 11/1975 | Vanlerberghe et al. ........ 424/70 |
| 3,929,990 A | 12/1975 | Green et al. ................. 424/78 |
| 3,966,904 A | 6/1976 | Green et al. ................. 424/78 |
| 4,001,432 A | 1/1977 | Green et al. ................ 424/329 |
| 4,005,193 A | 1/1977 | Green et al. ................ 424/168 |
| 4,013,787 A | 3/1977 | Varlerberghe et al. ........ 424/70 |
| 4,025,617 A | 5/1977 | Green et al. ................. 424/78 |
| 4,025,627 A | 5/1977 | Green et al. ............. 424/248.4 |
| 4,025,653 A | 5/1977 | Green et al. ................ 424/328 |
| 4,026,945 A | 5/1977 | Green et al. ................ 260/567 |
| 4,027,008 A | 5/1977 | Sokol ........................ 424/62 |
| 4,027,020 A | 5/1977 | Green et al. ........... 424/248.56 |
| 4,031,307 A | 6/1977 | DeMartino et al. ......... 536/114 |
| 4,131,576 A | 12/1978 | Iovine et al. ............... 260/174 |
| 4,157,388 A | 6/1979 | Christiansen ................ 424/70 |
| 4,172,887 A | 10/1979 | Vanlerberghe et al. ........ 424/70 |
| 4,223,009 A | 9/1980 | Chakrabarti ................ 424/47 |
| 4,277,581 A | 7/1981 | Vanlerberghe et al. ...... 529/420 |
| 4,349,532 A | 9/1982 | Vanlerberghe et al. ........ 424/47 |
| 4,390,689 A | 6/1983 | Jacquet et al. .............. 578/335 |
| 4,591,610 A | 5/1986 | Grollier ........................ 524/55 |
| 4,608,250 A | 8/1986 | Jacquet et al. ................ 424/71 |
| 4,702,906 A | 10/1987 | Jacquet et al. ................ 424/70 |
| 4,719,282 A | 1/1988 | Nadolsky et al. ........... 528/310 |
| 4,761,273 A | 8/1988 | Grollier et al. ............... 424/47 |
| 4,839,166 A | 6/1989 | Grollier et al. ............... 424/71 |
| 4,996,059 A | 2/1991 | Grollier et al. ............... 424/71 |
| 5,009,880 A | 4/1991 | Grollier et al. ............... 424/47 |
| 5,139,037 A | 8/1992 | Grollier et al. ............. 132/203 |
| 5,196,189 A | 3/1993 | Jacquet et al. ................ 424/72 |
| 5,914,373 A | 6/1999 | Glancy et al. .............. 525/406 |
| 6,273,920 B1 * | 8/2001 | De La Mettrie et al. ....... 8/401 |

FOREIGN PATENT DOCUMENTS

| | | |
|---|---|---|
| EP | 0 080 976 | 6/1983 |
| EP | 0 122 324 | 10/1984 |
| EP | 0 337 354 | 10/1989 |
| EP | 0 958 807 | 11/1999 |
| FR | 1 400 366 | 4/1965 |
| FR | 1 492 597 | 8/1967 |
| FR | 1 583 363 | 10/1969 |
| FR | 2 077 143 | 10/1971 |
| FR | 0 080 759 | 11/1971 |
| FR | 2 162 025 | 7/1973 |
| FR | 2 190 406 | 1/1974 |
| FR | 2 270 846 | 12/1975 |
| FR | 2 280 361 | 2/1976 |
| FR | 2 252 840 | 6/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 413 907 | 8/1979 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 470 596 | 6/1991 |
| FR | 2 770 522 | 5/1999 |
| WO | WO 99/17724 | * 4/1999 ............ A61K/7/06 |

OTHER PUBLICATIONS

M. R. Porter, "Handbook of Surfactants", Blackie & Son, Ltd., Glasgow & London, 1991, pp. 116–178.

(List continued on next page.)

Primary Examiner—Brian P. Mruk
Assistant Examiner—Eisa Elhilo
(74) Attorney, Agent, or Firm—Finnegan, Henderson, Farabow, Garrett & Dunner, L.L.P.

(57) ABSTRACT

The present invention relates to a ready to use composition, a process and a kit for bleaching keratin fibers, and in particular human keratin fibers such as the hair, comprising at least one oxidizing agent and at least one thickening polymer with an aminoplast-ether skeleton. This novel composition, process and kit can be used to bleach hair without running or falls in viscosity over time.

68 Claims, No Drawings

OTHER PUBLICATIONS

English language Derwent Abstract of EP 0 080 976, Jun. 8, 1983.
English language Derwent Abstract of FR 2 077 143, Oct. 15, 1971.
English language Derwent Abstract of FR 2 080 759, Nov. 19, 1971.
English language Derwent Abstract of FR 2 320 330, Mar. 4, 1977.
English language Derwent Abstract of FR 2 336 434, Jul. 22, 1977.
English language Derwent Abstract of FR 2 770 552, May 7, 1999.
Co–pending Application No. 10/149,073; Attorney Docket No. 05725.1068–00000, Title: Oxidation Dye Composition For Keratin Fibres Containing a Thickening Polymer With an Ether Plastic Skeleton, Inventor(s) Delphine Allard et al., U.S. Filing Date: Jun. 7, 2002.

Co–pending Application No. 10/149,008—Attorney Docket No. 05725.1070–00000, Title: Composition for Permanent Bleaching or Deformation of Keratin Fibers Comprising a Thickened Polymer With an Aminoplastic Ether Skeleton, Inventor(s): Frédéric Legrand et al.

Co–pending Application No. 10/148,955—Attorney Docket No. 05725.1071–00000, Title: Direct Dyeing Composition for Keratinic Fibres Containing a Thickening Polymer With an Ether Skeleton, Inventor(s): Delphine Allard et al., U.S. Filing Date: Jun. 7, 2002.

* cited by examiner

COMPOSITION, PROCESS AND KIT FOR BLEACHING KERATIN FIBERS COMPRISING AT LEAST ONE THICKENING POLYMER WITH AN AMINOPLAST-ETHER SKELETON

The present invention relates to a composition for bleaching keratin fibers, and in particular human keratin fibers such as the hair, comprising at least one oxidizing agent and at least one thickening polymer with an aminoplast-ether skeleton.

It is known practice to bleach keratin fibers, and in particular human hair, with bleaching compositions containing one or more oxidizing agents. Among the oxidizing agents conventionally used, mention may be made of hydrogen peroxide or compounds capable of producing hydrogen peroxide by hydrolysis, such as urea peroxide or persalts, for instance perborates, percarbonates and persulfates, hydrogen peroxide and persulfates being particularly preferred.

Said bleaching compositions are mainly in the form of anhydrous products (powders or creams) containing alkaline compounds (amines and alkali metal silicates) and a peroxygenated reagent such as ammonium or alkali metal persulfates, perborates or percarbonates, which are diluted at the time of use with an aqueous hydrogen peroxide composition. The bleaching compositions may also result from the mixing, at the time of use, of the anhydrous powder of peroxygenated reagent with an aqueous composition. containing the alkaline compounds and another aqueous composition containing hydrogen peroxide.

The bleaching compositions are also in the form of thickened aqueous hydrogen peroxide compositions, ready for use.

For the purposes of the invention, the term "ready-to-use composition" is understood as meaning the composition intended to be applied in unmodified form to keratin fibers, that is to say that said composition can be stored in unmodified form before use or result from the extemporaneous mixing of two or more compositions.

To localize the bleaching product on application to the hair so that it does not run down the face or beyond the areas which it is proposed to bleach, use has been made hitherto of conventional thickeners such as crosslinked polyacrylic acid, hydroxyethylcelluloses, certain polyurethanes, waxes and also, in the case of aqueous bleaching compositions, mixtures of nonionic surfactants with an HLB (Hydrophilic-Lipophilic Balance) value, which, when suitably chosen, give rise to the gelling effect when they are diluted with water and/or surfactants.

However, the Applicant has found that the thickening systems mentioned above do not make it possible to obtain bleaching results that are sufficiently powerful and homogeneous, and leave the hair coarse. Moreover, the Applicant has also found that ready-to-use bleaching compositions containing the oxidizing agent(s) and also the thickener systems of the prior art do not allow a sufficiently precise application without running or falls in viscosity over time.

However, after considerable research conducted in this matter, the Applicant has now discovered that it is possible to obtain ready-to-use bleaching compositions that do not run and thus remain satisfactorily localized at the point of application, and that also make it possible to obtain powerful and homogeneous bleaching results while at the same time leaving the hair less coarse, if an effective amount of a polymer with an aminoplast-ether skeleton is introduced into the composition.

These discoveries form the basis of the present invention.

One subject of the present invention is thus a ready-to-use composition for bleaching keratin fibers, in particular human keratin fibers such as the hair, comprising, in a medium that is suitable for bleaching, at least one oxidizing agent, which is characterized in that it also contains at least one polymer with an aminoplast-ether skeleton.

According to the invention, said composition is anhydrous or aqueous.

When the ready-to-use composition according to the invention results from the mixing, extemporaneously, of several compositions, the polymer containing an aminoplast-ether skeleton may be present in one or more or in all of the mixed compositions.

As a result, the polymer containing an aminoplast-ether skeleton may be present in an anhydrous composition in the form of a powder, preferably a pulverulent powder, or in the form of a cream and/or in one or more aqueous compositions.

Preferably, according to the invention, the polymer containing an aminoplast-ether skeleton is present in at least one aqueous composition that is mixed, at the time of use, with an anhydrous composition in the form of a powder or cream containing at least one oxidizing agent.

Even more preferably, one of these aqueous compositions mixed with the anhydrous composition contains hydrogen peroxide.

The invention is also directed toward a process for bleaching keratin fibers, and in particular human keratin fibers such as the hair, which uses the ready-to-use bleaching composition as described according to the invention.

The invention is also directed toward bleaching devices or wrapping "kits" containing such a ready-to-use composition.

Thus, a two-compartment device comprises a first compartment containing at least one powder or one anhydrous cream or an aqueous composition, and the second compartment contains an aqueous composition, at least one of the two compartments containing at least one oxidizing agent and at least one of the two compartments containing at least one polymer with an aminoplast-ether skeleton.

Another multicompartment "kit" may consist of a first compartment containing a powder or an anhydrous cream and two other compartments each containing an aqueous composition, at least one of the three compartments containing at least one oxidizing agent and at least one of the three compartments containing at least one polymer with an aminoplast-ether skeleton.

However, other characteristics, aspects, subjects and advantages of the invention will emerge even more clearly on reading the description and the examples that follow.

For the purposes of the present invention, the term "aminoplast-ether" means any product derived from the condensation of an aldehyde with an amine or an amide.

For the purposes of the present invention, the term "aminoplast-ether" also means any structural unit formed from an aminoplast residue and a divalent hydrocarbon-based residue linked to the aminoplast residue via an ether bond.

The polymers with an aminoplast-ether skeleton that are used according to the invention are preferably chosen from those containing at least one unit of structure (I) below:

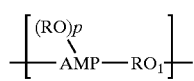 (I)

in which:

AMP is an aminoplast residue with alkylene units,

R denotes a hydrogen atom, a $C_1$–$C_4$ alkyl radical or a $C_1$–$C_4$ acyl radical, $RO_1$ is a divalent alkyleneoxy residue, p denotes a positive integer, the group(s) OR being linked to the alkylene units of the AMP residue.

Preferably, the polymers with an aminoplast-ether skeleton are chosen from those containing at least one unit of structure (II) below:

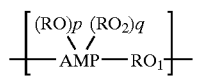 (II)

in which:

AMP, R, $RO_1$ and p have the same meaning as above, $RO_2$ is a hydrophobic group other than RO linked to AMP via a hetero atom and comprising at least two carbon atoms, and q is a positive integer.

Even more preferably, the polymers of the invention are of formulae (III) and (IIIa) below:

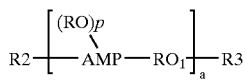 (III)

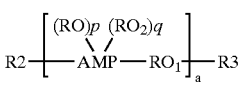 (IIIa)

in which:

AMP, R, $RO_1$, $RO_2$, p and q have the same meaning as above, R2 or R3, which may be identical or different, represent an end group that can denote a hydrogen atom, a group $RO_1H$, a group $RO_2H$, a group AMP(OR)p or any monofunctional group such as alkyl, cycloalkyl, aryl, aralkyl, alkylaryl, alkyloxyalkyl, aryloxyalkyl or cycloalkoxyalkyl, a being a number greater than 1 and preferably greater than 2.

The aminoplast residues bearing the groups OR thereof integrated into the polymers of the invention may be chosen, in a nonlimiting manner, from structures (IV) to (XV) below:

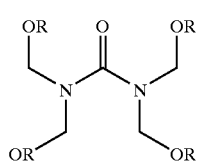 (IV)

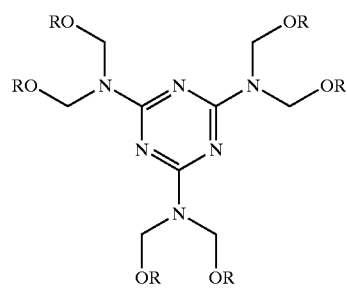 (V)

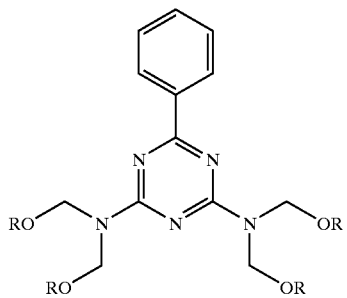 (VI)

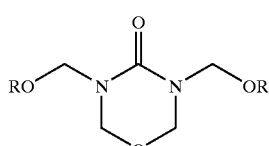 (VII)

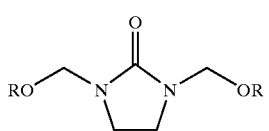 (VIII)

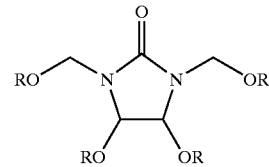 (IX)

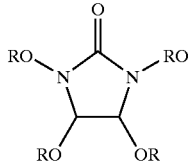 (X)

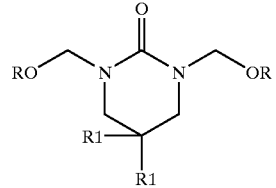 (XI)

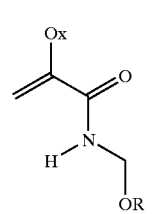 (XII)

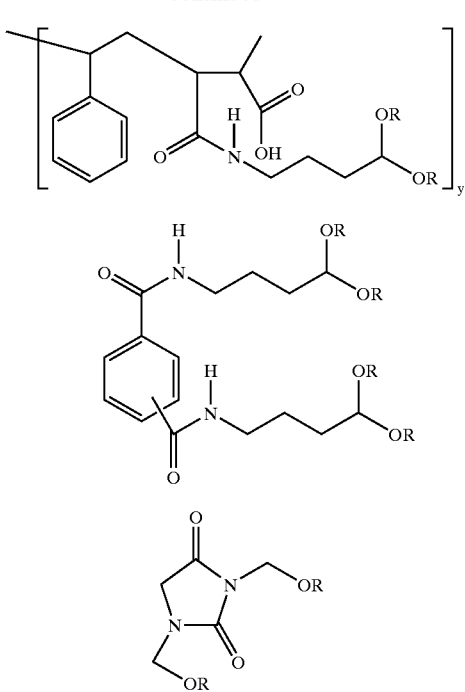

in which:
 R has the same meaning as above,
 R1 denotes $C_1$–$C_4$ alkyl,
 y is a number at least equal to 2,
 x denotes 0 or 1.

Preferably, the aminoplast residue(s) bearing the groups OR thereof is (are) chosen from those of structure (XVI) below:

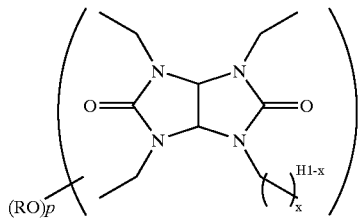

in which R, p and x have the same meanings as above.

The divalent alkyleneoxy residues are preferably those corresponding to the diols of general formula (XVII) below:

HO—(ZO)y-(Z1(Z2O)w)t-(Z'O)y'-Z3OH        (XVII), y and y' being numbers ranging from 0 to 1000,
t and w being numbers ranging from 0 to 10,
Z, Z', Z2 and Z3 are $C_2$–$C_4$ alkylene radicals and preferably radicals —CH2-CH(Z4)- and —CH2-CH(Z4)—CH2-,
Z1 being a linear or cyclic, branched or unbranched, aromatic or nonaromatic radical optionally comprising one or more hetero atoms containing from 1 to 40 carbon atoms,
Z4 denoting a hydrogen atom or a $C_1$–$C_4$ alkyl radical or a $C_1$–$C_3$ acyl radical, it being understood that at least one of the radicals Z4 of the radicals Z, Z', Z2 and Z3 is other than acyl.

Preferably, Z4 denotes a hydrogen atom or a methyl radical.

Even more preferably, t=0 and Z, Z' and Z3 denote —CH2CH2-, and at least one of the groups from among y and y' is other than 0. The compounds of formula (XVII) are then polyethylene glycols.

The polymers of formula (I) according to the invention are described in particular in U.S. Pat. No. 5,914,373, the content of which forms an integral part of the invention.

As polymers with an aminoplast-ether skeleton of formula (I), mention may be made in particular of the products Pure-Thix L [PEG-180/Octoxynol-40/TMMG Copolymer (INCI name)], Pure-Thix M [PEG-180/Laureth-50/TMMG Copolymer (INCI name)] and Pure-Thix HH [Polyether-1 (INCI name)] sold by the company Sud-Chemie.

The polymers with an aminoplast-ether skeleton are preferably used in an amount that can range from about 0.01% to 10% by weight relative to the total weight of the ready-to-use dye composition. More preferably, this amount ranges from about 0.1% to 5% by weight.

The oxidizing agents that may be used according to the invention are preferably chosen from hydrogen peroxide and compounds that release hydrogen peroxide by hydrolysis, such as urea peroxide and persalts.

Persalts that may be used according to the invention include persulfates and perborates and in particular sodium persulfate or potassium persulfate.

Other oxidizing agents that may be mentioned are chlorites.

It is also possible to use an enzymatic system that generates oxidizing species and in particular hydrogen peroxide. Examples of such enzymatic systems that may be mentioned include two-electron oxidoreductases combined with their donor in the presence of air, and more particularly the uricase, uric acid and air system.

Organic peroxides may also be used.

The hydrogen peroxide concentration of the ready-to-use compositions may range from 2 to 40 volumes. That of the other oxidizing compounds including, in particular, the compounds capable of forming hydrogen peroxide by hydrolysis, can range from 0.1% to 25% by weight approximately relative to the total weight of the composition.

The composition according to the invention may also contain direct dyes in addition to the oxidizing agents defined above. These direct dyes may then be chosen especially from nitro dyes, azo dyes and anthraquinone dyes, whether they are neutral, acidic or cationic.

More particularly, the compositions according to the invention can also contain at least one cationic or amphoteric substantive polymer.

For the purposes of the present invention, the expression "cationic polymer" denotes any polymer containing cationic groups and/or groups that can be ionized into cationic groups.

The cationic polymers that can be used in accordance with the present invention may be chosen from any of those already known per se as improving the cosmetic properties of the hair, i.e. in particular those described in patent application EP-A-337 354 and in French patents FR-2 270 846, 2 383 660, 2 598 611, 2 470 596 and 2 519 863.

The preferred cationic polymers are chosen from those which contain units containing primary, secondary, tertiary and/or quaternary amine groups which can either form part of the main polymer chain or which can be carried by a lateral substituent that is directly attached thereto.

The cationic polymers used generally have a number-average molecular mass of between 500 and $5 \times 10^6$ approximately, and preferably between $10^3$ and $3 \times 10^6$ approximately.

Among the cationic polymers, mention may be made more particularly of polymers of poly(quaternary ammonium), polyamino amide and polyamine type. These are known products. They are described in particular in French patents Nos. 2 505 348 or 2 542 997. Among said polymers, mention may be made of:

(1) Homopolymers or copolymers derived from acrylic or methacrylic esters or amides and comprising at least one of the units of formula (I), (II), (III) or (IV) below:

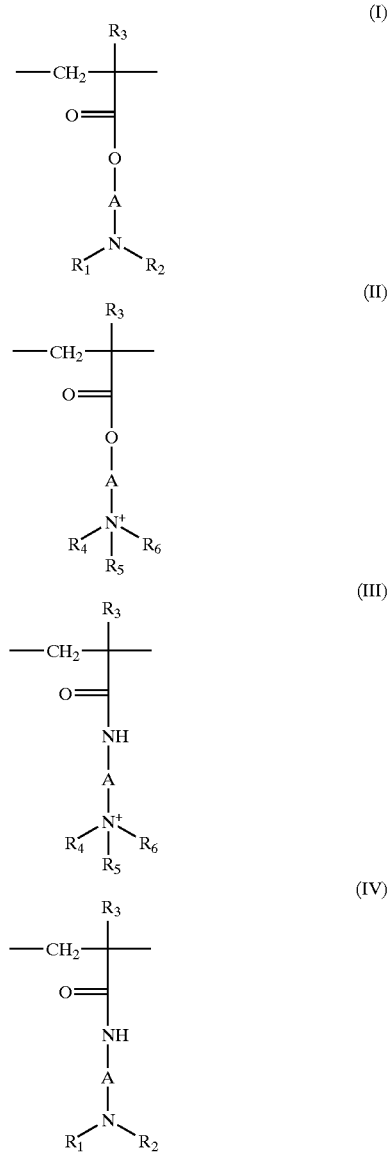

in which:

$R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl;

X denotes an anion derived from an inorganic or organic acid, such as a methosulfate anion or a halide such as chloride or bromide.

Polymers of family (1) can also contain one or more units derived from comonomers which may be chosen from the family of acrylamides, methacrylamides, diacetone acrylamides, acrylamides and methacrylamides substituted on the nitrogen with lower ($C_1$–$C_4$) alkyls, acrylic or methacrylic acids or esters thereof, vinyllactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba Geigy, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name "Gafquat" by the company ISP, such as, for example, "Gafquat 734" or "Gafquat 755", or alternatively the products known as "Copolymer 845, 958 and 937". These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, and quaternized vinylpyrrolidone/dimethylaminopropylmethacrylamide copolymers such as the product sold under the name "Gafquat HS 100" by the company ISP.

(2) The cellulose ether derivatives containing quaternary ammonium groups, described in French patent 1 492 597, and in particular polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose that has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the names "Celquat L 200" and "Celquat H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example. Such products are sold in particular under the trade names Jaguar C13 S, Jaguar C 15, Jaguar C 17 or Jaguar C162 by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylamino-hydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (V) or (VI):

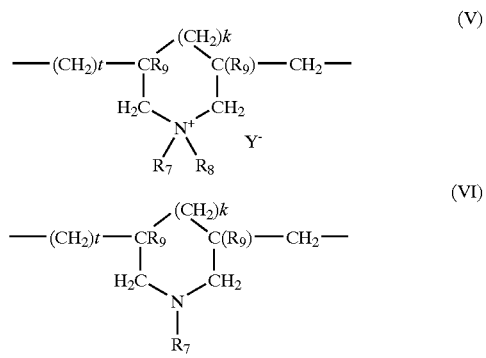

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 22 carbon atoms, a hydroxyalkyl group in which the alkyl group preferably has 1 to 5 carbon atoms, a lower $C_1$–$C_4$ amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group containing from 1 to 4 carbon atoms; $Y^+$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallyl-ammonium chloride homopolymer sold under the name "Merquat 100" by the company Calgon (and its homologues of low weight-average molecular mass) and copolymers of diallyldimethylammonium chloride and of acrylamide, sold under the name "Merquat 550".

(10) The quaternary diammonium polymer containing repeating units corresponding to the formula:

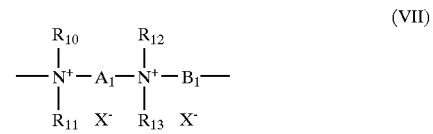

in which formula (VII):

$R_{10}$, $R_{11}$, $R_{12}$ and $R_{13}$, which may be identical or different, represent aliphatic, alicyclic or arylaliphatic radicals- .containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$–$C_6$ alkyl radical substituted with a nitrile, ester, acyl or amide group or a group —CO—O—$R_{14}$—D or —CO—NH—$R_{14}$—D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and

(11) Poly(quaternary ammonium) polymers consisting of units of formula (IX):

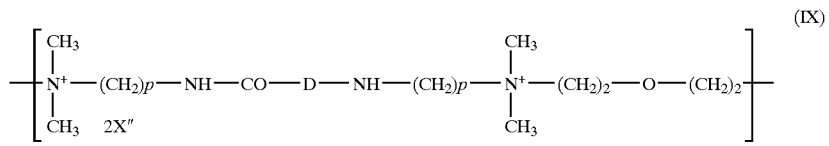

$X^-$ denotes an anion derived from an inorganic or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO—D—OC—$(CH_2)_n$— in which D denotes:

a) a glycol residue of formula: —O—Z—O—, where Z denotes a linear or branched hydrocarbon radical or a group corresponding to one of the following formulae:

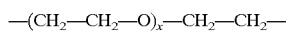

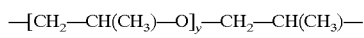

where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon radical, or alternatively the divalent radical

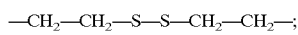

d) a ureylene group of formula: —NH—CO—NH—.

Preferably, $X^-$ is an anion such as chloride or bromide.

These polymers generally have a number-average molecular mass of between 1000 and 100,000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the formula (VIII) below:

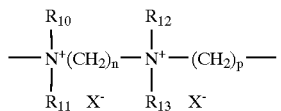

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and $X^-$ is an anion derived from a mineral or organic acid.

in which:

p denotes an integer ranging from 1 to 6 approximately,

D can be zero or can represent a group —$(CH_2)_r$—CO— in which r denotes a number equal to 4 or 7, and $X^-$ is an anion derived from a mineral or organic acid.

The cationic polymers comprising units of formula (IX) are disclosed in particular in patent application EP-A-122 324 and may be prepared according to the processes disclosed in U.S. Pat. Nos. 4,157,388, 4,390,689, 4,702,906 and 4,719,282.

Among these polymers, the ones that are preferred are those with a molecular mass, measured by carbon-13 NMR, of less than 100000, and in the formula of which:

p is equal to 3, and a) D represents a group —$(CH_2)_4$—CO—, X denotes a chlorine atom, the molecular mass, measured by carbon-13 NMR ($C^{13}$ NMR), being about 5600; a polymer of this type is proposed by the company Miranol under the name Mirapol-AD1, b) D represents a group —$(CH_2)_7$—CO— and X denotes a chlorine atom, the molecular mass, measured by carbon-13 NMR ($C^{13}$ NMR), being about 8100; a polymer of this type is proposed by the company Miranol under the name Mirapol-AZ1, c) D denotes the value zero and X denotes a chlorine atom, the molecular mass, measured by carbon-13 NMR ($C^{13}$ NMR), being about 25500; a polymer of this type is sold by the company Miranol under the name Mirapol-A15, d) a "block copolymer" formed from units corresponding to the polymers described in paragraphs a) and c), sold by the company Miranol under the names Mirapol-9 ($C^{13}$ NMR molecular mass of about 7800), Mirapol-175 ($C^{13}$ NMR molecular mass of about 8000) and Mirapol-95 ($C^{13}$ NMR molecular mass of about 12500).

Even more particularly, the polymer which is preferred according to the invention is a polymer containing units of formula (IX) in which p is equal to 3, D denotes the value zero and X denotes a chlorine atom, the molecular mass, measured by carbon-13 NMR ($C^{13}$ NMR), being about 25500.

(12) Quaternary polymers of vinylpyrrolidone and of vinylimidazole, such as, for example, the products sold under the names Luviquat FC 905, FC 550 and FC 370 by the company BASF.

(13) Polyamines such as Polyquart H sold by Henkel under the reference name "Polyethylene glycol (15) tallow polyamine" in the CTFA dictionary.

(14) Crosslinked methacryloyloxy($C_1$–$C_4$)alkyltri-($C_1$–$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl-ammonium chloride copolymer (20/80 by weight) in the form of a dispersion containing 50% by weight of said copolymer in mineral oil can be used more particularly. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which can be used in the context of the present invention, it is preferred to use the polymers of families (1), (9), (10), (11) and (14) and even more preferably the polymers of formulae (W) and (U) below:

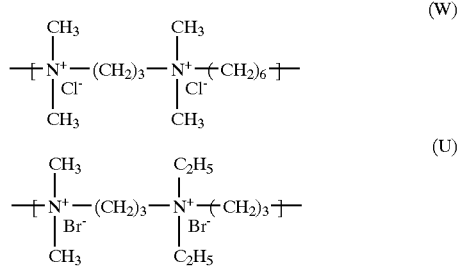

and in particular those in which the molecular weight, determined by gel permeation chromatography, is between 9500 and 9900;
and in particular those in which the molecular weight, determined by gel permeation chromatography, is about 1200.

The concentration of cationic polymer in the compositions according to the present invention can range from 0.01% to 10% by weight relative to the total weight of the composition, preferably from 0.05% to 5% and even more preferably from 0.1% to 3%.

The film-forming amphoteric polymers which can be used in accordance with the present invention can be chosen from polymers containing units K and M distributed randomly in the polymer chain, in which K denotes a unit derived from a monomer containing at least one basic nitrogen atom and M denotes a unit derived from an acid monomer containing one or more carboxylic or sulfonic groups, or alternatively K and M can denote groups derived from carboxybetaine or sulfobetaine zwitterionic monomers;

K and M can also denote a cationic polymer chain containing primary, secondary, tertiary or quaternary amine groups, in which at least one of the amine groups bears a carboxylic or sulfonic group connected via a hydrocarbon radical or alternatively K and M form part of a chain of a polymer containing an α,β-dicarboxylic ethylene unit in which one of the carboxylic groups has been made to react with a polyamine containing one or more primary or secondary amine groups.

The amphoteric polymers corresponding to the definition given above which are more particularly preferred are chosen from the following polymers:

(1) Polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537. Mention may also be made of the sodium acrylate/acrylamidopropyltrimethylammonium chloride copolymer sold under the name Polyquart KE 3033 by the company Henkel.

The vinyl compound can also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.

(2) Polymers containing units derived from:
  a) at least one monomer chosen from acrylamides and methacrylamides substituted on the nitrogen with an alkyl radical,
  b) at least one acidic comonomer containing one or more reactive carboxylic groups, and
  c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which are more particularly preferred according to the invention are groups in which the alkyl radicals contain from 2 to 12 carbon atoms and more particularly N-ethylacrylamide, N-tert-butylacryl-amide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer or Lovocryl 47 by the company National Starch are particularly used.

(3) Crosslinked and alkylated polyamino amides partially or totally derived from polyamino amides of general formula:

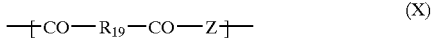

in which $R_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of said acids to a bis(primary) or bis(secondary) amine, and Z denotes a bis(primary), mono- or bis(secondary) polyalkylene-polyamine radical and preferably represents:

a) in proportions of from 60 to 100 mol %, the radical

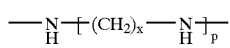 (XI)

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (XI) above in which x=2 and p=1 and which is derived from ethylenediamine, or the radical derived from piperazine:

c) in proportions of from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the alkylation are preferably propane sultone or butane sultone, the salts of the alkylating agents are preferably the sodium or potassium salts.

(4) Polymers containing zwitterionic units of formula:

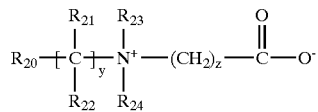 (XII)

in which $R_{20}$ denotes a polymerizable unsaturated group such as an acrylate, methacrylate, acrylamide or methacrylamide group, y and z represent an integer from 1 to 3, $R_{21}$ and $R_{22}$ represent a hydrogen atom, methyl, ethyl or propyl, $R_{23}$ and $R_{24}$ represent a hydrogen atom or an alkyl radical such that the sum of the carbon atoms in $R_{23}$ and $R_{24}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/dimethyl-carboxymethylammonio ethyl methacrylate such as the product sold under the name Diaformer Z301 by the company Sandoz.

(5) Polymers derived from chitosan containing monomer units corresponding to the following formulae (XIII), (XIV) and (XV):

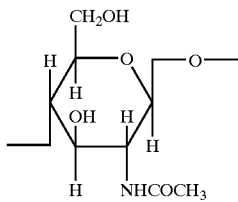 (XIII)

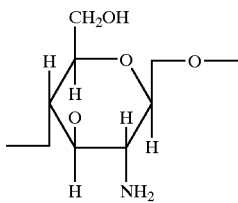 (XIV)

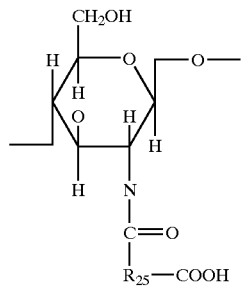 (XV)

the unit (XIII) being present in proportions of between 0 and 30%, the unit (XIV) in proportions of between 5 and 50% and the unit F in proportions of between 30 and 90%, it being understood that, in this unit (XV), $R_{25}$ represents a radical of formula:

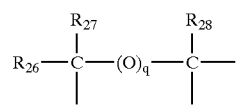

in which if q=0, $R_{26}$, $R_{27}$ and $R_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals $R_{26}$, $R_{27}$ and $R_{28}$ being, in this case, a hydrogen atom;

or, if q=1, $R_{26}$, $R_{27}$ and $R_{28}$ each represent a hydrogen atom, as well as the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula (XI) such as those described, for example, in French patent 1 400 366:

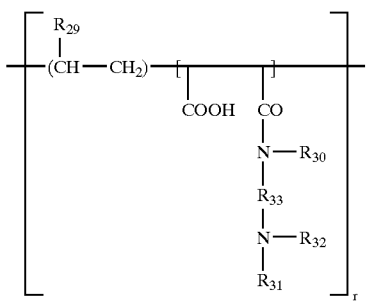

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: $-R_{33}-N(R_{31})_2$, $R_{33}$ representing a $-CH_2-CH_2-$, $-CH_2-CH_2-CH_2-$ or $-CH_2-CH(CH_3)-$ group, $R_{31}$ having the meanings mentioned above, as well as the higher homologues of these radicals and containing up to 6 carbon atoms.

(8) Amphoteric polymers of the type $-D-X-D-X-$ chosen from:

a) polymers obtained by the action of chloroacetic acid or sodium chloroacetate on compounds containing at least one unit of formula:

$$-D-X-D-X-D- \qquad (XVII)$$

where D denotes a radical

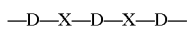

and X denotes the symbol E or E', E or E', which may be identical or different, denoting a divalent radical which is an alkylene radical containing a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) Polymers of formula:

$$-D-X-D-X- \qquad (XVIII)$$

in which D denotes a radical

and

X denotes the symbol E or E' and at least once E';

E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) $(C_1-C_5)$alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric polymers that are particularly preferred according to the invention are those of family (1).

According to the invention, the amphoteric polymer(s) can represent from 0.01% to 10% by weight, preferably from 0.05% to 5% by weight and even more preferably from 0.1% to 3% by weight, relative to the total weight of the composition.

The compositions of the invention preferably comprise one or more surfactants.

The surfactant(s) can be chosen without preference, alone or as mixtures, from anionic, amphoteric, nonionic, zwitterionic and cationic surfactants.

The surfactants that are suitable for carrying out the present invention are, in particular, the following:

(i) Anionic surfactant(s):

As examples of anionic surfactants which can be used, alone or as mixtures, in the context of the present invention, mention may be made in particular (nonlimiting list) of salts (in particular alkaline salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; $(C_6-C_{24})$ alkyl sulfosuccinates, $(C_6-C_{24})$ alkyl ether sulfosuccinates, $(C_6-C_{24})$ alkylamide sulfosuccinates; $(C_6-C_{24})$ alkyl sulfoacetates; $(C_6-C_{24})$ acyl sarcosinates and $(C_6-C_{24})$ acyl glutamates. It is also possible to use the carboxylic esters of $(C_6-C_{24})$ alkylpolyglycosides, such as alkylglucoside citrates, alkypolyglycoside tartrates and alkypolyglycoside sulfosuccinates, alkylsulfosuccinamates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Alkyl-D-galactosideuronic acids and their salts, polyoxyalkylenated $(C_6-C_{24})$ alkyl ether carboxylic acids, polyoxyalkylenated $(C_6-C_{24})$ alkylaryl ether carboxylic acids, polyoxyalkylenated $(C_6-C_{24})$ alkylamido ether carboxylic acids and their salts, in particular those containing from 2 to 50 alkylene oxide, in particular ethylene oxide, groups, and mixtures thereof can also be used.

(ii) Nonionic surfactant(s):

The nonionic surfactants are also compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (non-limiting list) polyethoxylated or polypropoxylated alkylphenols, α-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as $(C_{10}-C_4)$alkylamine oxides or N-acylaminopropylmorpholine oxides. It will be noted that the alkylpolyglycosides constitute nonionic surfactants that are particularly suitable in the context of the present invention.

(iii) Amphoteric or zwitterionic surfactant(s):

The amphoteric or zwitterionic surfactants, whose nature is not a critical feature in the context of the present invention, can be, in particular (non-limiting list), aliphatic secondary or tertiary amine derivatives in which the aliphatic radical is a linear or branched chain containing 8 to 18 carbon atoms and containing at least one water-soluble anionic group (for example carboxylate, sulfonate, sulfate, phosphate or phosphonate); mention may also be made of $(C_8-C_{20})$alkylbetaines, sulfobetaines, $(C_8-C_{20})$alkylamido$(C_1-C_6)$alkylbetaines or $(C_8-C_{20})$alkylamido$(C_1-C_6)$alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names amphocarboxyglycinates and amphocarboxypropionates of respective structures:

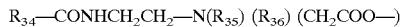

$R_{34}$—CONHCH$_2$CH$_2$—N($R_{35}$) ($R_{36}$) (CH$_2$COO—)

in which: $R_{34}$ denotes an alkyl radical derived from an acid $R_{34}$—COOH present in hydrolyzed coconut oil, a heptyl, nonyl or undecyl radical, $R_{35}$ denotes a β-hydroxyethyl group and $R_{36}$ denotes a carboxymethyl group; and

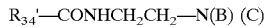

$R_{34}'$—CONHCH$_2$CH$_2$—N(B) (C)

in which:
B represents —CH$_2$CH$_2$OX', C represents —(CH$_2$)$_z$—Y', with z=1 or 2, X' denotes the —CH$_2$CH$_2$—COOH group or a hydrogen atom, Y'denotes —COOH or the —CH$_2$—CHOH—SO$_3$H radical, $R_{34}'$ denotes an alkyl radical of an acid $R_{37}$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold under the trade name Miranol® C2M Concentrate by the company Rhodia Chimie.

(iv) Cationic surfactants:

Among the cationic surfactants which may be mentioned in particular (nonlimiting list) are: primary, secondary or tertiary fatty amine salts, optionally polyoxyalkylenated; quaternary ammonium salts such as tetraalkylammonium, alkylamidoalkyl-trialkylammonium, trialkylbenzylammonium, trialkylhydroxyalkylammonium or alkylpyridinium chlorides or bromides; imidazoline derivatives; or amine oxides of cationic nature.

The amounts of surfactants present in the ready-to-use composition according to the invention can range from 0.01% to 40% and preferably from 0.1% to 30% relative to the total weight of the composition.

The compositions according to the invention can also contain other agents for adjusting the rheology, such as cellulosic thickeners (hydroxyethylcellulose, hydroxypropylcellulose, carboxymethylcellulose, etc.), guar gum and its derivatives (hydroxypropyl guar, etc.), gums of microbial origin (xanthan gum, scleroglucan gum, etc.), synthetic thickeners such as crosslinked acrylic acid or acrylamidopropanesulfonic acid homopolymers and ionic or nonionic associative polymers such as the polymers sold under the names Pemulen TR1 or TR2 by the company Goodrich, Salcare SC90 by the company Allied Colloids, Aculyn 22, 28, 33, 44 or 46 by the company Rohm & Haas, and Elfacos T210 and T212 by the company Akzo.

These additional thickeners can represent from 0.05% to 10% by weight relative to the total weight of the composition.

The compositions according to the invention also advantageously contain an alkaline agent.

Among the basifying agents that may be mentioned, for example, are aqueous ammonia, ammonium chloride, alkali metal or alkaline-earth metal carbonates, alkali metal or alkaline-earth metal silicates, alkali metal or alkaline-earth metal phosphates, alkanolamines such as monoethanolamine, diethanolamine and triethanolamine and also derivatives thereof, sodium hydroxide, potassium hydroxide and the compounds of formula (XIX) below:

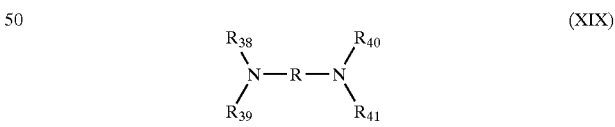

in which R is a propylene residue optionally substituted with a hydroxyl group or a $C_1-C_4$ alkyl radical; $R_{38}$, $R_{39}$, $R_{40}$ and $R_{41}$, which may be identical or different, represent a hydrogen atom, a $C_1-C_4$ alkyl radical or a $C_1-C_4$ hydroxyalkyl radical.

The compositions of the invention may also contain sequestering agents such as, for example, ethylenediaminetetraacetic acid (EDTA).

When the compositions containing the oxidizing agent and the polymer with an aminoplast-ether skeleton are in anhydrous form (powder or cream), they contain the main agents and additives mentioned above in the form of solids or liquids that are essentially anhydrous. They may also contain mineral or organic fillers such as silica or clays. They may also contain binders such as vinylpyrrolidone, oils or waxes, polyalkylene glycols and polyalkylene glycol derivatives. They may also contain lubricants, for instance polyol stearates or alkali metal or alkaline-earth metal stearates, and also colorants or matt-effect agents, for instance titanium oxides.

When the medium containing the oxidizing agent is an aqueous medium, it may optionally contain cosmetically acceptable organic solvents including, more particularly, alcohols such as ethyl alcohol, isopropyl alcohol, benzyl alcohol and phenylethyl alcohol, or glycols or glycol ethers such as, for example, ethylene glycol monomethyl, monoethyl and monobutyl ethers, propylene glycol or its ethers such as, for example, propylene glycol monomethyl ether, butylene glycol, dipropylene glycol and also diethylene glycol alkyl ethers such as, for example, diethylene glycol monoethyl ether or monobutyl ether, in concentrations of between about 0.5% and 20% and preferably between about 2% and 10% by weight relative to the total weight of the composition.

The bleaching composition according to the invention [lacuna] also contain an effective amount of other agents, which are previously known elsewhere for bleaching, such as various common adjuvants, for instance volatile or nonvolatile, cyclic or linear or branched silicones, which are organomodified (especially with amine groups) or not organomodified, preserving agents, ceramides, plant, mineral or synthetic waxes or oils, acids and in particular AHAs, etc.

Needless to say, a person skilled in the art will take care to select the optional additional compound(s) mentioned above such that the advantageous properties intrinsically associated with the bleaching composition according to the invention are not, or are not substantially, adversely affected by the envisioned addition(s).

The pH of the ready-to-use composition is generally between the values 4 and 12. It is preferably between 7 and 11.5 and even more preferably between 8 and 11.

The bleaching process according to the invention preferably consists in applying the ready-to-use oxidizing composition to wet or dry keratin fibers, and leaving the composition to act for an exposure time preferably ranging from 1 to 60 minutes approximately, and more preferably from 10 to 45 minutes approximately, rinsing the fibers and then optionally washing them with shampoo, followed by rinsing them again and drying them.

Concrete examples illustrating the invention are given below, without, however, having any limiting nature.

EXAMPLE 1

The ready-to-use aqueous bleaching composition below was prepared (expressed in grams):

| 200-volumes hydrogen peroxide | 12 |
|---|---|
| Stabilizer | qs |
| Pure-Thix-HH | 0.3 AM* |
| (INCI = Polyether-1) | |
| pH agent qs | pH 4.7 |
| Water qs | 100 |

AM* = active material

The above bleaching composition was applied to natural hair under a hood, and left for 45 minutes, then rinsed thoroughly with water. A uniform lightening of the hair was obtained.

EXAMPLE 2

The bleaching composition below was prepared (expressed in grams):

| Anhydrous composition | |
|---|---|
| Potassium persulfate | 35 |
| Sodium persulfate | 30 |
| Sodium metasilicate | 14 |
| Ammonium chloride | 5 |
| EDTA | 1 |
| Sodium dioctylsulfosuccinate/ sodium benzoate | 1 |
| Calcium stearate | 1 |
| Pure-Thix-HH (INCI = Polyether-1) | 3 |
| Silica | 7 |

40 g of the above anhydrous composition were mixed with 80 g of the following aqueous composition:

| Aqueous composition | |
|---|---|
| Cetearyl alcohol/ceteareth 30 | 2.85 |
| Stabilizers | 0.06 |
| Sequestering agent | 0.15 |
| 200-volumes hydrogen peroxide | 9 |
| Phosphoric acid qs | pH 2 |
| Distilled water qs | 100 |

A ready-to-use bleaching cream was thus obtained, which, when applied and left for 45 minutes under a hood, gave an intense and homogeneous bleaching of natural dark hair.

What is claimed is:

1. A ready-to-use composition for bleaching keratin fibers comprising, in a medium that is suitable for bleaching, at least one oxidizing agent, and at least one thickening polymer with an aminoplast-ether skeleton.

2. A composition of claim 1, wherein the at least one thickening polymer comprises at least one unit of structure (I):

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue; and p is a positive integer;

RO is a hydrophobic group linked to the alkylene units of the AMP residue.

3. A composition of claim 1, wherein the at least one thickening polymer comprises at least one unit of structure (II):

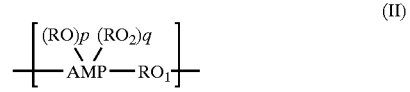

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

RO is a hydrophobic group linked to the alkylene units of the AMP residue;

$RO_2$ is hydrophobic group, other than RO, linked to AMP via a hetero atom and comprising at least two carbon atoms; and p and q are positive integers.

4. A composition of claim 1, wherein the at least one thickening polymer comprises at least one unit of structure (III) or (IIIa):

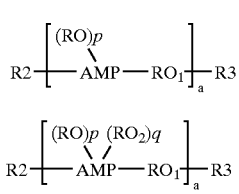

wherein:

AMP is an aminoplast residue with alkylene units;

R is chosen from a hydrogen atom, a $C_1$–$C_4$ alkyl radical, and a $C_1$–$C_4$ acyl radical;

$RO_1$ is a divalent alkyleneoxy residue;

RO is a hydrophobic group linked to the alkylene units of the AMP residue;

$RO_2$ is hydrophobic group, other than RO, linked to AMP via a hetero atom and comprising at least two carbon atoms;

p and q are positive integers;

R2 or R3, which may be identical or different, represent an end group that can denote a hydrogen atom, an $RO_1H$ group, an $RO_2H$ group, an AMP(OR)p group or any monofunctional group; and a is a number greater than 1.

5. A composition of claim 4, wherein said monofunctional group is chosen from alkyl, cycloalkyl, aryl, aralkyl, alkylaryl, alkyloxyalkyl, aryloxyalkyl, and cycloalkoxyalkyl.

6. A composition of claim 2, wherein said at least one aminoplast residue is chosen from those of structures (IV) to (XV):

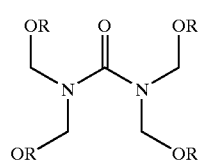

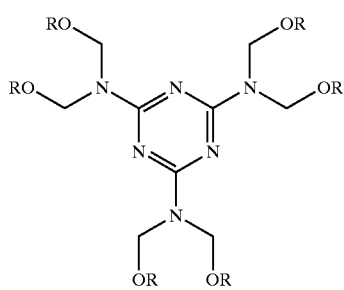

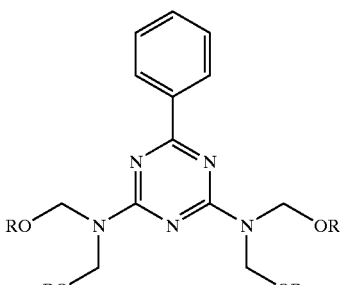

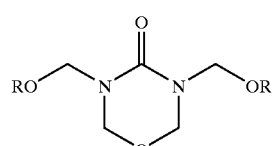

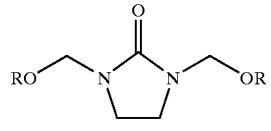

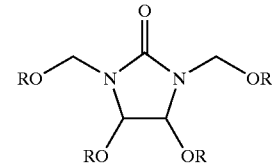

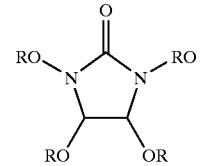

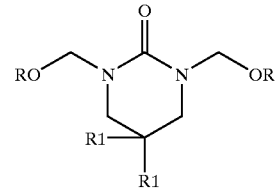

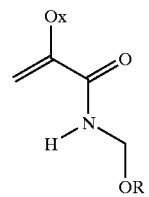

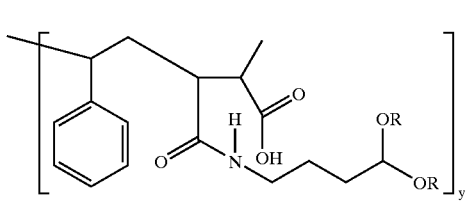
(XIII)
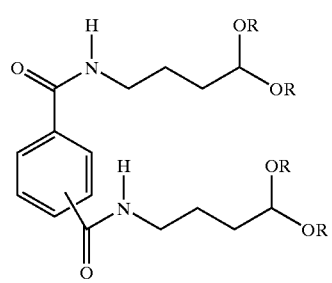
(XIV)
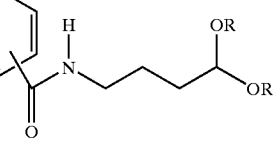
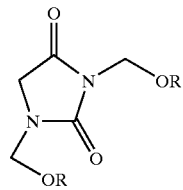
(XV)
wherein:
R is chosen from a hydrogen atom, a $C_1$–$C_4$ alkyl radical, and a $C_1$–$C_4$ acyl radical;
R1 is a $C_1$–$C_4$ alkyl;
y is a number at least equal to 2; and
x is 0 or 1.
7. A composition of claim 3, wherein said at least one aminoplast residue is chosen from those of structures (IV) to (XV):
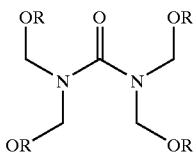
(IV)
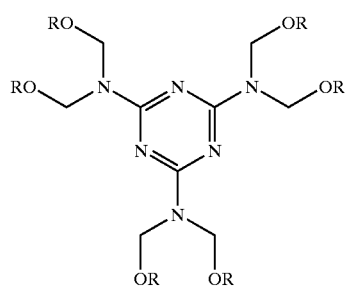
(V)
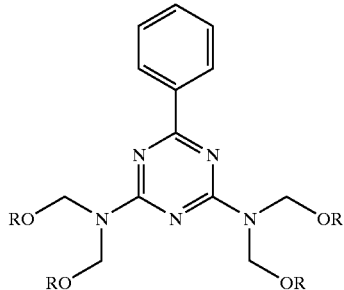
(VI)
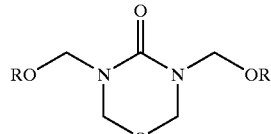
(VII)
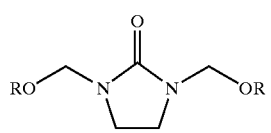
(VIII)
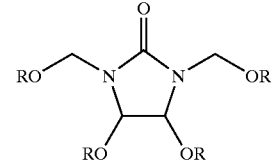
(IX)
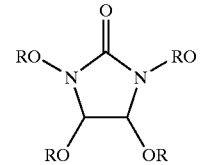
(X)
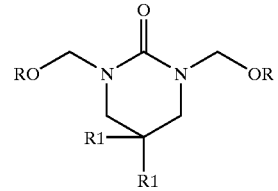
(XI)
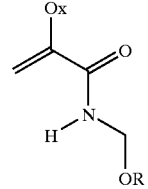
(XII)
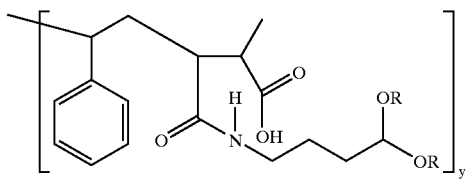
(XIII)

-continued
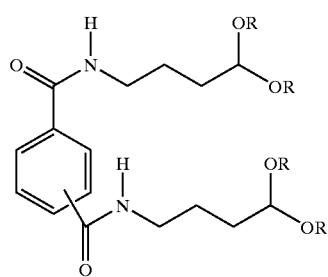
(XIV)
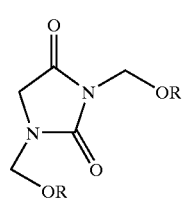
(XV)
wherein:
R is chosen from a hydrogen atom, a $C_1$–$C_4$ alkyl radical, and a $C_1$–$C_4$ acyl radical;
R1 is a $C_1$–$C_4$ alkyl;
y is a number at least equal to 2; and
x is 0 or 1.
8. A composition of claim 4, wherein said at least one aminoplast residue is chosen from those of structures (IV) to (XV):
(IV)
(V)
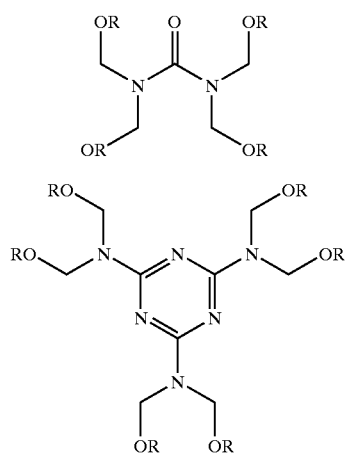
(VI)
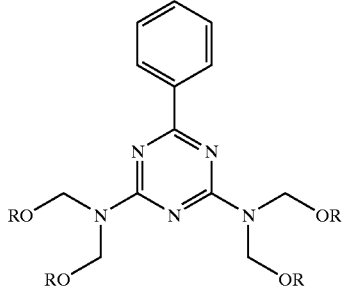
-continued
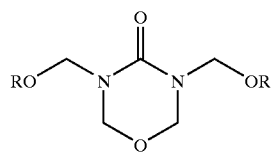
(VII)
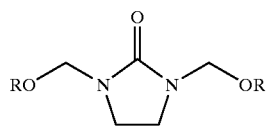
(VIII)
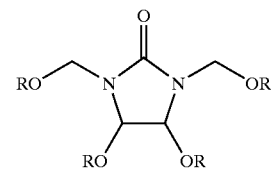
(IX)
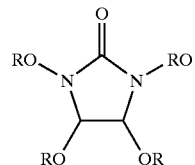
(X)
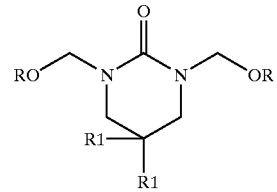
(XI)
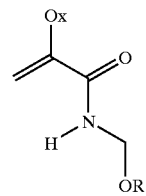
(XII)
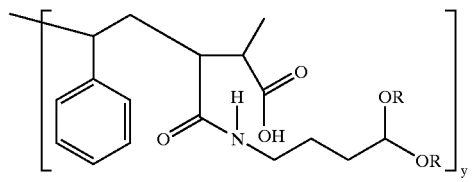
(XIII)
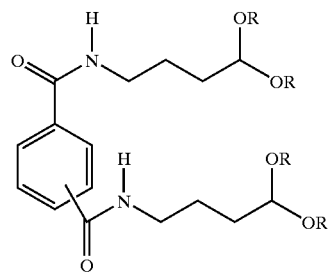
(XIV)

-continued

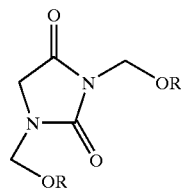
(XV)

wherein:

R is chosen from a hydrogen atom, a $C_1$–$C_4$ alkyl radical, and a $C_1$–$C_4$ acyl radical;

R1 is a $C_1$–$C_4$ alkyl;

y is a number at least equal to 2; and x is 0 or 1.

9. A composition of claim 2, wherein said at least one aminoplast residue corresponds to structure (XVI):

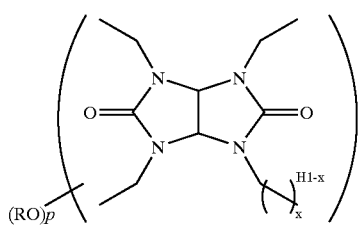
(XVI)

wherein:

R is chosen from a hydrogen atom, a $C_1$–$C_4$ alkyl radical, and a $C_1$–$C_4$ acyl radical;

p is a positive integer; and x is 0 or 1.

10. A composition of claim 3, wherein the at least one aminoplast residue corresponds to structure (XVI):

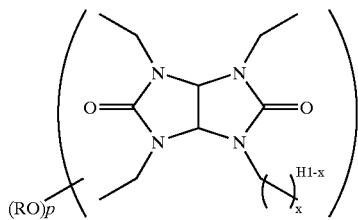
(XVI)

wherein:

R is chosen from a hydrogen atom, a $C_1$–$C_4$ alkyl radical, and a $C_1$–$C_4$ acyl radical;

p is a positive integer; and x is 0 or 1.

11. A composition of claim 4, wherein the at least one aminoplast residue corresponds to structure (XVI):

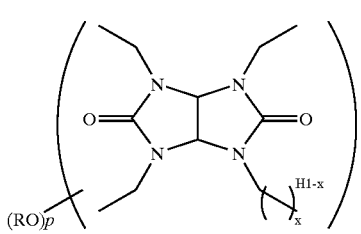
(XVI)

wherein:

R is chosen from a hydrogen atom, a $C_1$–$C_4$ alkyl radical, and a $C_1$–$C_4$ acyl radical;

p is a positive integer; and x is 0 or 1.

12. A composition of claim 2, wherein the alkyleneoxy residue corresponds to the diols of general formula (XVII):

$$HO-(ZO)y-(Z1(Z2O)w)t-(Z'O)y'-Z3OH \quad (XVII)$$

wherein:

y and y' are numbers ranging from 0 to 1000;

t and w are numbers ranging from 0 to 10;

Z, Z', Z2 and Z3 are $C_2$–$C_4$ alkylene radicals;

Z1 is a linear or cyclic, branched or unbranched, aromatic or nonaromatic radical optionally comprising one or more hetero atoms containing from 1 to 40 carbon atoms.

13. A composition of claim 3, wherein the alkyleneoxy residue corresponds to the diols of general formula (XVII):

$$HO-(ZO)y-(Z1(Z2O)w)t-(Z'O)y'-Z3OH \quad (XVII)$$

wherein:

y and y' are numbers ranging from 0 to 1000;

t and w are numbers ranging from 0 to 10;

Z, Z', Z2 and Z3 are $C_2$–$C_4$ alkylene radicals;

Z1 is chosen from a linear or cyclic, branched or unbranched, aromatic or nonaromatic radical optionally comprising one or more hetero atoms containing from 1 to 40 carbon atoms.

14. A composition of claim 4, wherein the alkyleneoxy residue corresponds to the diols of general formula (XVII):

$$HO-(ZO)y-(Z1(Z2O)w)t-(Z'O)y'-Z3OH \quad (XVII)$$

wherein:

y and y' are numbers ranging from 0 to 1000;

t and w are numbers ranging from 0 to 10;

Z, Z', Z2 and Z3 are $C_2$–$C_4$ alkylene, radicals; and

Z1 is chosen from a linear or cyclic, branched or unbranched, aromatic or nonaromatic radical optionally comprising one or more hetero atoms containing from 1 to 40 carbon atoms.

15. A composition of claim 12, wherein Z, Z', Z2 and Z3 are radicals chosen from —CH2-CH(Z4)- and —CH2-CH(Z4)-CH2-, wherein Z4 is chosen from a hydrogen atom, a $C_1$–$C_4$ alkyl radical, and a $C_1$–$C_3$ acyl radical, wherein at least one of the radicals Z4 is other than acyl.

16. A composition of claim 12, wherein Z, Z', Z2 and Z3 are radicals chosen from —CH2-CH(Z4)- and —CH2-CH(Z4)-CH2-, wherein at least one of the radicals Z4 is chosen from a hydrogen atom and a methyl radical.

17. A composition of claim 13, wherein Z, Z', Z2 and Z3 are radicals chosen from —CH2-CH(Z4)- and —CH2-CH (Z4)-CH2-, wherein Z4 is chosen from a hydrogen atom, a C₁–C₄ alkyl radical, and a C₁–C₃ acyl radical, wherein at least one of the radicals Z4 is other than acyl.

18. A composition of claim 13, wherein Z, Z', Z2 and Z3 are radicals chosen from —CH2-CH(Z4)- and —CH2-CH(Z4)-CH2-, wherein at least one of the radicals Z4 is chosen from a hydrogen atom and a methyl radical.

19. A composition of claim 14, wherein Z, Z', Z2 and Z3 are radicals chosen from —CH2-CH(Z4)- and —CH2-CH(Z4)-CH2-, wherein Z4 is chosen from a hydrogen atom, a C₁–C₄ alkyl radical, and a C₁–C₃ acyl radical, wherein at least one of the radicals Z4 is other than acyl.

20. A composition of claim 14, wherein Z, Z', Z2 and Z3 are radicals chosen from —CH2-CH(Z4)- and —CH2-CH(Z4)-CH2-, wherein at least one of the radicals Z4 is chosen from a hydrogen atom and a methyl radical.

21. A composition of claim 12, wherein t=0; Z, Z' and Z3 denote —CH2CH2-; and at least one of y and y' being other than 0.

22. A composition of claim 13, wherein t=0; Z, Z' and Z3 denote —CH2CH2-; and at least one of y and y' being other than 0.

23. A composition of claim 14, wherein t=0; Z, Z' and Z3 denote —CH2CH2-; and at least one of y and y' being other than 0.

24. A composition of claim 1, wherein the at least one thickening polymer is chosen from PEG-180/Octoxynol-40/TMMG Copolymer, PEG-180/Laureth-50/TMMG Copolymer, and Polyether-1.

25. A composition of claim 1, wherein the at least one thickening polymer is present in an amount ranging from 0.01% to 10% by weight relative to the total weight of the composition.

26. A composition of claim 25, wherein the at least one thickening polymer is present in an amount ranging from 0.1% to 5% by weight relative to the total weight of the composition.

27. A composition of claim 1, wherein the at least one oxidizing agent is chosen from hydrogen peroxide and compounds that release hydrogen peroxide by hydrolysis.

28. A composition of claim 27, wherein the compounds that release hydrogen peroxide by hydrolysis include urea peroxide and persalts, chlorites, enzymatic systems that generate oxidizing species and organic peroxides.

29. A composition of claim 28, wherein the persalt is an alkali metal or alkaline-earth metal persulfate or perborate.

30. A composition of claim 28, wherein the enzymatic system is a two-electron oxidoreductase combined with its donor in the presence of air.

31. A composition of claim 30, wherein the oxidoreductase is uricase and its donor is uric acid.

32. A composition of claim 27, wherein the hydrogen peroxide concentration ranges from 2 to 40 volumes.

33. A composition of claim 27, wherein the concentration of oxidizing agent ranges from 0.1% to 25% by weight relative to the total weight of the composition.

34. A composition of claim 1, further comprising at least one direct dye.

35. A composition of claim 1, further comprising at least one cationic or amphoteric polymer.

36. A composition of claim 35, wherein the at least one cationic polymer is a poly(quaternary ammonium) polymer consisting of repeating units corresponding to formula (W):

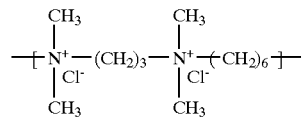

37. A composition of claim 35, wherein the at least one cationic polymer is a poly(quaternary ammonium) polymer consisting of repeating units corresponding to formula (U):

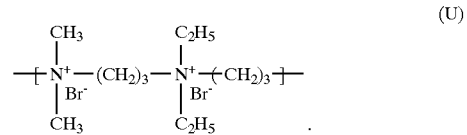

38. A composition of claim 35, wherein the at least one amphoteric polymer is a copolymer comprising, as monomers, acrylic acid and a dimethyldiallylammonium salt.

39. A composition of claim 35, wherein the at least one cationic or amphoteric polymer is present in an amount ranging from 0.01% to 10% by weight relative to the total weight of the composition.

40. A composition of claim 39, wherein the at least one cationic or amphoteric polymer is present in an amount ranging from 0.05% to 5% by weight relative to the total weight of the composition.

41. A composition of claim 40, wherein the at least one cationic or amphoteric polymer is present in an amount ranging from 0.1% to 3% by weight relative to the total weight of the composition.

42. A composition of claim 1, further comprising at least one surfactant that is anionic, cationic, nonionic or amphoteric.

43. A composition of claim 42, wherein the at least one surfactant is present in an amount ranging from 0.01% to 40% by weight relative to the total weight of the composition.

44. A composition of claim 43, wherein the at least one surfactant is present in an amount ranging from 0.1% to 30% by weight relative to the total weight of the composition.

45. A composition of claim 1, further comprising at least one additional thickener.

46. A composition of claim 45, wherein the at least one additional thickener is a cellulose derivative, a guar derivative, a gum of microbial origin or a synthetic thickener.

47. A composition of claim 45, wherein the at least one additional thickener is present in an amount ranging from 0.05% to 10% by weight relative to the total weight of the composition.

48. A composition of claim 1, further comprising at least one alkaline agent in an amount ranging from 0.05% to 30% by weight relative to the total weight of the composition.

49. A composition of claim 48, wherein the at least one alkaline agent is chosen from aqueous ammonia, ammonium chloride, alkali metal or alkaline-earth metal carbonates, alkali metal or alkaline-earth metal silicates, alkali metal or alkaline-earth metal phosphates, alkanolamines, sodium hydroxide, potassium hydroxide, and the compounds of formula (XIX):

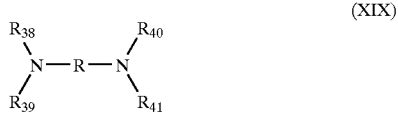 (XIX)

wherein R is a propylene residue optionally substituted with a hydroxyl group or a $C_1$–$C_4$ alkyl radical;

$R_{38}$, $R_{39}$, $R_{40}$ and $R_{41}$, which may be identical or different, is chosen from a hydrogen atom, a $C_1$–$C_4$ alkyl radical, and a $C_1$–$C_4$ hydroxyalkyl radical.

50. A composition of claim 49, wherein said alkanolamines is chosen from at least one of monoethanolamine, diethanolamine, triethanolamine, and derivatives thereof.

51. A composition for bleaching keratin fibers obtained by extemporaneous mixing, at the time of use of at least one anhydrous composition containing at least one oxidizing agent, and of at least one aqueous composition, wherein at least one of the anhydrous and aqueous compositions contain at least one thickening polymer with an aminoplast-ether skeleton.

52. A composition of claim 51, wherein the at least one anhydrous composition is in pulverulent form.

53. A composition of claim 51, wherein the at least one anhydrous composition contains at least one additive chosen from mineral or organic fillers, binders, lubricants, and colorants or matt-effect agents.

54. A composition of claim 53, wherein said mineral or organic fillers are silica or clays, said binders are vinylpyrrolidone, oils or waxes, polyalkylene glycols or polyalkylene glycol derivatives, said lubricants are polyol stearates or alkali metal or alkaline-earth metal stearates, and said colorants or matt-effect agents are titanium oxides.

55. A composition of claim 53, wherein each of the at least one additives is present in an amount ranging from 0% to 30% by weight relative to the total weight of the composition.

56. A composition of claim 1, wherein the composition is aqueous.

57. A composition of claim 56, wherein the composition comprises an aqueous medium which contains at least one organic solvent.

58. A composition of claim 57, wherein the at least one organic solvent is present in an amount ranging from 0.5% to 20% by weight relative to the total weight of the composition.

59. A composition of claim 58, wherein the at least one organic solvent is present in a amount ranging from 2% to 10% by weight relative to the total weight of the composition.

60. A composition of claim 57, wherein the aqueous medium contains hydrogen peroxide.

61. A composition of claim 1, wherein the composition has a pH ranging from 4 to 12.

62. A composition of claim 61, wherein the composition has a pH ranging from 7 to 11.5.

63. A composition of claim 62, wherein the composition has a pH ranging from 8 to 11.

64. A composition of claim 51, wherein the at least one thickening polymer with an aminoplast-ether skeleton is in an aqueous composition.

65. A process for bleaching keratin fibers comprising, applying a ready-to-use composition to wet or dry fibers, in a medium that is suitable for bleaching, wherein the medium contains at least one oxidizing agent and at least one thickening polymer with an aminoplast-ether skeleton, and rinsing the fibers after leaving the composition to act for a time ranging from 1 to 60 minutes.

66. A process of claim 65, wherein the time ranges from 1 to 45 minutes.

67. A process of claim 65, further comprising washing the keratin fibers with shampoo followed by rinsing and drying the keratin fibers.

68. A two-compartment device or kit for bleaching keratin fibers, comprising a first compartment and a second compartment, wherein the first compartment contains at least one powder or at least one aqueous composition, and the second compartment contains at least one aqueous composition, at least one of the two compartments containing at least one oxidizing agent and at least one of the two compartments containing at least one thickening polymer with an aminoplast-ether skeleton.

* * * * *

UNITED STATES PATENT AND TRADEMARK OFFICE
CERTIFICATE OF CORRECTION

PATENT NO. : 6,800,096 B1  
DATED : October 5, 2004  
INVENTOR(S) : Legrand et al.

Page 1 of 1

It is certified that error appears in the above-identified patent and that said Letters Patent is hereby corrected as shown below:

Title page,  
Item [75], Inventors, "Billancourt" should read -- Boulogne Billancourt --.

Column 24,  
Lines 59-66, " 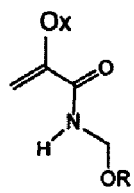 " should read 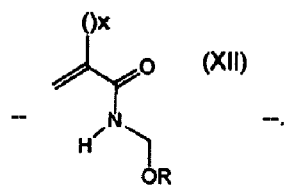 --.

Column 26,  
Lines 50-56, " 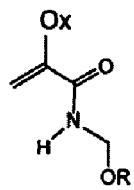 " should read 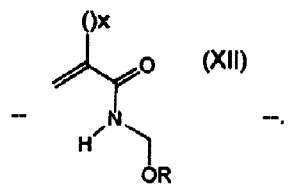 --.

Column 28,  
Lines 39-45, " 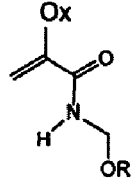 " should read 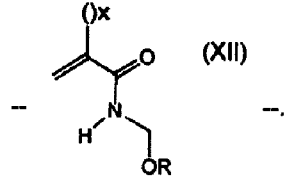 --.

Signed and Sealed this

Twelfth Day of April, 2005

JON W. DUDAS  
*Director of the United States Patent and Trademark Office*